(12) United States Patent
Prohens López et al.

(10) Patent No.: US 11,731,927 B2
(45) Date of Patent: Aug. 22, 2023

(54) COCRYSTALS OF UBIQUINOL AND COMPOSITIONS COMPRISING THEM

(71) Applicant: Center for Intelligent Research in Crystal Engineering, S.L., Palma de Mallorca (ES)

(72) Inventors: Rafel Prohens López, Sabadell (ES); Rafael Barbas Cañero, Santa Coloma de Gramenet (ES); Lidia Bofill Herrera, Bigues i Riells (ES); Dafne De Sande López, L'Hospitalet de Llobregat (ES)

(73) Assignee: CENTER FOR INTELLIGENT RESEARCH IN CRYSTAL ENGINEERING, S.L., Palma de Mallorca (ES)

( * ) Notice: Subject to any disclaimer, the term of this patent is extended or adjusted under 35 U.S.C. 154(b) by 114 days.

(21) Appl. No.: 16/969,869

(22) PCT Filed: Feb. 22, 2019

(86) PCT No.: PCT/EP2019/054420
§ 371 (c)(1),
(2) Date: Aug. 13, 2020

(87) PCT Pub. No.: WO2019/162429
PCT Pub. Date: Aug. 29, 2019

(65) Prior Publication Data
US 2020/0385327 A1     Dec. 10, 2020

(30) Foreign Application Priority Data
Feb. 23, 2018   (EP) ..................... 18382109

(51) Int. Cl.
C07C 43/23     (2006.01)
C07C 65/05     (2006.01)
A61K 45/06     (2006.01)

(52) U.S. Cl.
CPC .............. C07C 43/23 (2013.01); C07C 65/05 (2013.01); *A61K 45/06* (2013.01); *C07B 2200/13* (2013.01)

(58) Field of Classification Search
CPC ..... C07B 2200/13; A61K 45/06; C07C 43/23; C07C 65/05; C07C 41/58
See application file for complete search history.

(56) References Cited

U.S. PATENT DOCUMENTS

| | | | |
|---|---|---|---|
| 8,703,155 B2* | 4/2014 | Ueda | A61K 31/122 424/94.1 |
| 2007/0059356 A1* | 3/2007 | Almarsson | A61K 31/415 514/217 |
| 2014/0357661 A1* | 12/2014 | Bradbury | A61K 31/519 546/85 |
| 2015/0284311 A1 | 10/2015 | Kawachi et al. | |

FOREIGN PATENT DOCUMENTS

EP      2725004 A1    4/2014

* cited by examiner

*Primary Examiner* — Rosalynd A Keys
(74) *Attorney, Agent, or Firm* — Squire Patton Boggs (US) LLP

(57) ABSTRACT

The present invention relates to a cocrystal of ubiquinol and a hydrogen bond donor coformer, to a process for the preparation thereof, and to its use as a medicament or a dietary supplement. The invention also relates to compositions comprising the cocrystal.

16 Claims, 2 Drawing Sheets

COCRYSTALS OF UBIQUINOL AND COMPOSITIONS COMPRISING THEM

CROSS-REFERENCE TO RELATED APPLICATIONS

This application is a national-stage filing under 37 USC 371(c) of International Application No. PCT/EP2019/054420, filed Feb. 22, 2019, which claims priority to and the benefit of, European Patent Application EP18382109.9, filed on Feb. 23, 2018, the entire contents of each of which are herein incorporated by reference in their entirety for all purposes.

TECHNICAL FIELD

The present invention relates to cocrystals of ubiquinol, to processes for the preparation thereof, and to their use as a medicament or a dietary supplement. It also relates to compositions comprising them.

BACKGROUND ART

CoQ-10 (coenzyme Q-10) is a fat-soluble quinone commonly known as ubiquinone. Ubiquinone is found in most living organisms, and is essential for the production of cellular energy. Although it can be synthesized in the body situations may arise when the need for ubiquinone surpasses the body's ability to synthesize it. Ubiquinone can be derived from dietary sources, being often administered in a powdered form, as in a tablet or as a suspension. However, the bioavailability of ubiquinone is limited.

Ubiquinol is an reduced form of coenzyme $Q_{10}$ (also known as ubiquinone) and has the CAS No. 992-78-9. The redox functions of ubiquinol in cellular energy production and antioxidant protection are based on the ability to exchange two electrons in a redox cycle between ubiquinol (reduced) and the ubiquinone (oxidized) form. Taken orally, ubiquinol exhibits greater bioavailability than ubiquinone.

Health benefits of ubiquinol are known. Particularly, ubiquinol supports optimal heart health, supports natural cellular energy production, helps to prevent damage in the body caused by oxidative stress, and replenishes CoQ10 blood levels depleted by many cholesterol medicines. Ubiquinol is sold as a dietary supplement.

The structure of ubiquinol corresponds to the formula (I):

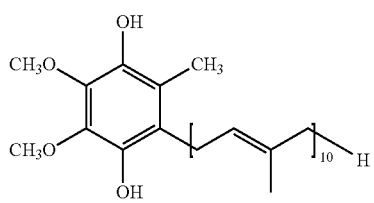

(I)

Ubiquinol may be prepared in crystallized form such as disclosed in US2015284311A1. The procedures disclosed therein results in crystalline Form I and Form II of ubiquinol. Nevertheless, ubiquinol is easily oxidized in the presence of oxygen and light, being converted back into ubiquinone. Thus, to minimize oxidation ubiquinol must be packaged, stored, and transported in a hermetically sealed container in a substantially air or oxygen free condition such as under an inert atmosphere.

It is known that different solid forms of a active ingredient can have different characteristics, and offer certain advantages, for example with regard to solubility or bioavailability. Thus, the discovery of new solid forms allows for improving the pharmacokinetic properties of the active ingredients and as a consequence the characteristics of the pharmaceutical formulations containing the active ingredients, since some forms are more adequate for one type of formulation, and other forms for other different formulations.

Particularly, in recent years cocrystal formation has emerged as a viable strategy towards improving the pharmacokinetic data of active ingredients. By cocrystallizing an active ingredient or a salt of an active ingredient with a coformer (the second component of the cocrystal), a new solid state form of the active ingredient is created having unique properties compared with existing solid forms of the active ingredient or its salts. Such different properties may provide a basis for improving formulation, for example, by facilitating better processing or handling characteristics, changing the dissolution profile in a favourable direction, or improving stability and shelf-life. However, cocrystal formation is not predictable, and in fact is not always possible. Moreover, there is no way to predict the properties of a particular cocrystal of a compound until it is formed. Finding the appropriate coformers and right conditions to obtain a particular cocrystal can take significant time, effort and resources.

From what is known in the art, there is still the need of finding new stable solid forms of ubiquinol in order to improve the pharmaceutical properties of the pharmaceutical formulations containing them.

SUMMARY OF INVENTION

The inventors have found that ubiquinol can form a cocrystal with a hydrogen bond donor coformer as defined herein below. The provision of the mentioned cocrystals of ubiquinol gives a new tool to overcome the problems associated with the stability of ubiquinol because it has been found that these cocrystals have a high stability at room temperature even when exposed to air, what makes it easier to handle. This property makes the cocrystals more suitable for preparing pharmaceutical or dietary compositions containing ubiquinol.

Cocrystal formation, particularly with a hydrogen bond donor coformer, cannot be predicted. No attempt to obtain cocrystals of ubiquinol has been found in the literature.

Accordingly, the provision of an improved crystal form of ubiquinol in the form of a cocrystal with a hydrogen bond donor coformer as defined herein below is considered a contribution to the art.

Thus, a first aspect of the invention refers to the provision of a cocrystal of ubiquinol and a hydrogen bond donor coformer.

A second aspect of the invention refers to a composition comprising an effective amount of the cocrystal of ubiquinol and a hydrogen bond donor coformer together, with one or more appropriate acceptable excipients or carriers.

Finally, a third aspect of the invention refers to a cocrystal of ubiquinol and a hydrogen bond donor coformer for use as a medicament.

DETAILED DESCRIPTION OF THE INVENTION

Figure 1:
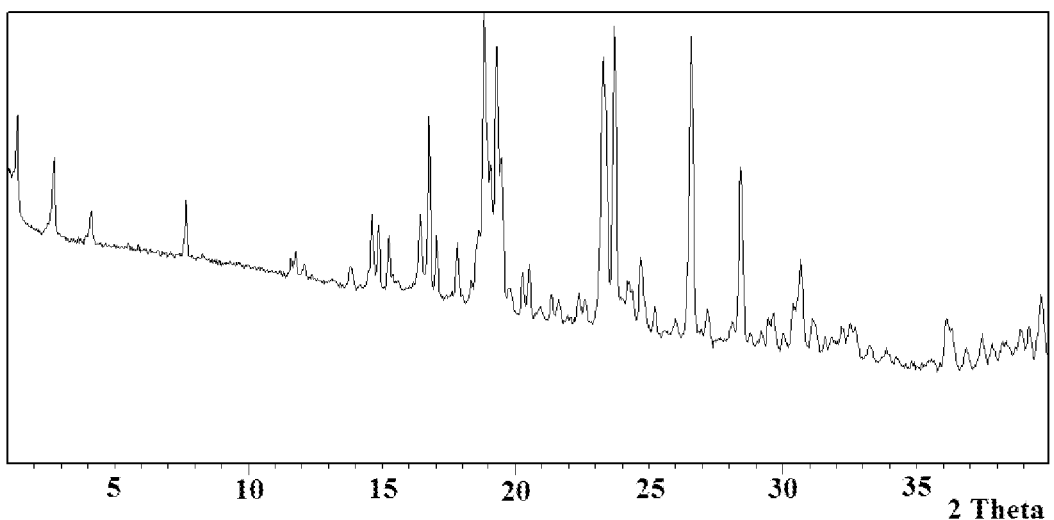
FIG. 1 shows the X-ray powder diffractogram (XRPD) of cocrystal of ubiquinol and 3-hydroxybenzoic acid. The diagram expresses intensity (I; counts) versus angle 2 theta (°).

All terms as used herein in this application, unless otherwise stated, shall be understood in their ordinary meaning as known in the art. Other more specific definitions for certain terms as used in the present application are as set forth below and are intended to apply uniformly throughout the specification and claims unless an otherwise expressly set out definition provides a broader definition.

For the purposes of the present invention, ranges given, such as of temperatures, times, and the like, should be considered approximate, unless specifically stated.

For the purposes of the invention, the term "cocrystal" refers herein to a crystalline entity with at least two different components constituting the unit cell at room temperature (20-25° C.) and interacting by intermolecular interactions. Thus, in a cocrystal, one component crystallizes together with one or more neutral components. The cocrystals may include one or more solvent molecules in the crystal lattice. Thus, the term "cocrystal hydrate" or "hydrate cocrystal" have the same meaning and are used interchangeable. They refer to a cocrystal including water as a solvent in the crystal lattice.

The expression "cocrystal obtainable by" is used here to define each specific cocrystal of the invention by the process for obtaining it and refers to the product obtainable by any of the corresponding processes disclosed herein. For the purposes of the invention the expressions "obtainable", "obtained" and equivalent expressions are used interchangeably and, in any case, the expression "obtainable" encompasses the expression "obtained".

When values of characteristic peaks of an X-ray diffractogram are given it is said that these are "approximate" values. It should be understood that the values are the ones shown in the corresponding lists or tables±0.3 degrees 2 theta measured in an X-ray diffractometer with Cu—K$_\alpha$ radiation λ=1.5406 Å.

When a ratio of components of the cocrystals of the invention is specified it refers to the molar ratio between the components that forms the cocrystal. The term "molar ratio" has been used to express the stoichiometric amount in moles of each of the components of a cocrystal. The molar ratio can be determined by $^1$H NMR (Proton nuclear magnetic resonance), thermogravimetric analysis (TGA) or single crystal X-ray diffraction (SCXRD). When values of molar ratio are given according to TGA it is said that these are "approximate" values due to the measurement error. It should be understood that when a molar ratio is mentioned, it corresponds to a molar ratio±0.2%. The variability of the results is due to the inherent sensibility of the TGA equipment.

The term "room temperature" refers to a temperature of the environment, without heating or cooling, and is generally comprised from 20° C. to 25° C.

The term "overnight" refers to a time interval comprised from 10 h to 20 h.

The term "alkyl" refers to a saturated straight, or branched hydrocarbon chain which contains the number of carbon atoms specified in the description or claims. Examples include, among others, the group methyl, ethyl, propyl, isopropyl, butyl, isobutyl, sec-butyl, and tert-butyl.

As mentioned above, the first aspect of the invention is the provision of a cocrystal of ubiquinol and a hydrogen bond donor coformer.

In an embodiment, the hydrogen bond donor coformer is selected from the group consisting of an organic carboxylic acid, an organic alcohol, and urea.

The term "organic carboxylic acid" refers to a pharmaceutically acceptable organic acid containing at least one —COOH group. In an embodiment, the cocrystal of ubiquinol is one wherein the hydrogen bond donor coformer is an organic carboxylic acid selected from a compound of $R_1$—$(COOH)_n$ and

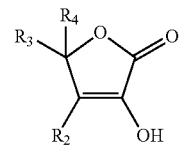

wherein: $R_1$ is selected from the group consisting of $(C_1$-$C_6)$alkyl, $(C_2$-$C_6)$alkenyl, and $(C_2$-$C_6)$alkinyl being optionally substituted by one or more hydroxyl groups; $R_2$ is selected from the group consisting of H and OH; $R_3$ is selected from the group consisting of H and —COOH; $R_4$ is a $(C_1$-$C_6)$alkyl; and n is an integer selected from 1 to 3. Particularly, the hydrogen bond donor coformer is a benzoic acid such as 3-hydroxybenzoic acid, 3,4-dihydroxybenzoic acid, 3,5-dihydroxybenzoic acid, and 2,5-dihydroxybenzoic acid.

In a particular embodiment, the benzoic acid is 3-hydroxybenzoic acid, and the cocrystal of ubiquinol and 3-hydroxybenzoic acid is characterized by having an X-ray powder diffractogram that comprises characteristic peaks at approximately 1.36, 2.74 and 4.12±0.3 degrees 2 theta (Cu—K$_\alpha$ radiation, λ=1.5406 Å). In an embodiment, the cocrystal of ubiquinol and 3-hydroxybenzoic acid is characterized by having an X-ray powder diffractogram that comprises further characteristic peaks at 17.04, 17.81, 19.30 and 23.28±0.3 degrees 2 theta (Cu—K$_\alpha$ radiation, λ=1.5406 Å).

More specifically, the cocrystal of ubiquinol and 3-hydroxybenzoic acid of the invention is characterized by exhibiting in the X-ray powder diffractogram a pattern of peaks, expressed in 2 theta units in degrees, 2 (°), which is shown in Table 1.

TABLE 1

List of selected peaks (only peaks with relative intensity greater than or equal to 1% are indicated):

| Pos. [2θ] | Rel. Int. [%] |
|---|---|
| 1.36 | 42.55 |
| 2.74 | 25.70 |
| 4.12 | 9.54 |
| 11.56 | 3.88 |
| 11.76 | 5.34 |
| 12.08 | 2.89 |

TABLE 1-continued

List of selected peaks (only peaks with relative intensity greater than or equal to 1% are indicated):

| Pos. [2θ] | Rel. Int. [%] |
| --- | --- |
| 13.83 | 3.78 |
| 14.62 | 17.55 |
| 14.87 | 14.60 |
| 15.25 | 12.33 |
| 17.04 | 13.54 |
| 17.81 | 12.45 |
| 18.84 | 100.00 |
| 19.30 | 86.12 |
| 20.53 | 9.26 |
| 22.39 | 4.37 |
| 22.62 | 3.38 |
| 23.28 | 80.74 |
| 23.41 | 50.98 |
| 24.40 | 5.99 |
| 27.20 | 4.75 |
| 28.43 | 41.89 |
| 29.65 | 4.86 |
| 30.37 | 6.76 |
| 32.19 | 4.15 |
| 32.53 | 4.70 |
| 32.71 | 4.15 |

The cocrystal of ubiquinol and 3-hydroxybenzoic acid of the invention may be further characterized by an X-ray diffractogram as in FIG. 1.

In another embodiment, the benzoic acid is 3,4-dihydroxybenzoic acid, and the cocrystal of ubiquinol and 3,4-dihydroxybenzoic acid is characterized by having an X-ray powder diffractogram that comprises characteristic peaks at approximately 1.34, 2.69 and 4.04±0.3 degrees 2 theta (Cu—K$_\alpha$ radiation, λ=1.5406 Å). In an embodiment, the cocrystal of ubiquinol and 3,4-dihydroxybenzoic acid of the invention is characterized by having an X-ray powder diffractogram that comprises further characteristic peaks at 14.60, 17.29, and 18.06±0.3 degrees 2 theta (Cu—K$_\alpha$ radiation, λ=1.5406 Å).

More specifically, the cocrystal of ubiquinol and 3,4-dihydroxybenzoic acid of the invention is characterized by exhibiting in the X-ray powder diffractogram a pattern of peaks, expressed in 2 theta units in degrees, 2 (°), which is shown in Table 2.

TABLE 2

List of selected peaks (only peaks with relative intensity greater than or equal to 1% are indicated):

| Pos. [°2θ] | Rel. Int. [%] |
| --- | --- |
| 1.34 | 85.44 |
| 2.69 | 42.92 |
| 4.04 | 13.34 |
| 6.70 | 2.21 |
| 8.07 | 2.30 |
| 11.65 | 4.00 |
| 11.97 | 3.85 |
| 13.66 | 2.73 |
| 14.60 | 13.20 |
| 15.20 | 7.27 |
| 15.49 | 3.64 |
| 17.29 | 9.23 |
| 18.06 | 12.46 |
| 18.80 | 44.25 |
| 19.09 | 100.00 |
| 20.07 | 3.83 |
| 20.73 | 5.35 |
| 23.09 | 90.48 |
| 23.68 | 4.78 |
| 24.07 | 6.29 |

TABLE 2-continued

List of selected peaks (only peaks with relative intensity greater than or equal to 1% are indicated):

| Pos. [°2θ] | Rel. Int. [%] |
| --- | --- |
| 27.60 | 5.25 |
| 30.35 | 5.61 |
| 30.68 | 4.78 |
| 32.48 | 2.92 |
| 32.89 | 4.52 |
| 38.13 | 2.94 |
| 38.50 | 3.75 |

Figure 2:
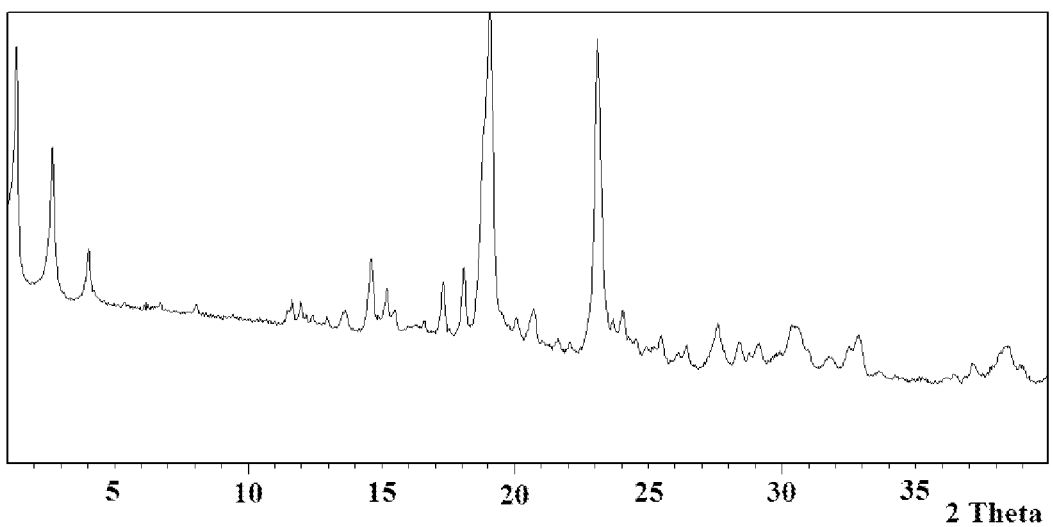
FIG. 2 shows the X-ray powder diffractogram (XRPD) of cocrystal hydrate of ubiquinol and 3,4-dihydroxybenzoic acid. The diagram expresses intensity (I; counts) versus angle 2 theta (°).

The cocrystal of ubiquinol and 3,4-dihydroxybenzoic acid of the invention may be further characterized by an X-ray diffractogram as in FIG. 2.

In an embodiment, the cocrystal of ubiquinol and 3,4-dihydroxybenzoic acid is a hydrate cocrystal. More particularly, the cocrystal is a hydrate with a 1.6%±0.1% water content according to TGA analysis.

In another embodiment, the benzoic acid is 3,5-dihydroxybenzoic acid, and the cocrystal of ubiquinol and 3,5-dihydroxybenzoic acid is characterized by having an X-ray powder diffractogram that comprises characteristic peaks at approximately 1.37, 2.75 and 4.13±0.3 degrees 2 theta (Cu—K$_\alpha$ radiation, λ=1.5406 Å). In an embodiment, the cocrystal of ubiquinol and a 3,5-dihydroxybenzoic acid of the invention is characterized by having an X-ray powder diffractogram that comprises further characteristic peaks at 16.23, 16.90, 17.67 and 19.22±0.3 degrees 2 theta (Cu—K$_\alpha$ radiation, λ=1.5406 Å).

More specifically, the cocrystal of ubiquinol and 3,5-dihydroxybenzoic acid of the invention is characterized by exhibiting in the X-ray powder diffractogram a pattern of peaks, expressed in 2 theta units in degrees, 2 (°), which is shown in Table 3.

TABLE 3

List of selected peaks (only peaks with relative intensity greater than or equal to 1% are indicated):

| Pos. [°2θ] | Rel. Int. [%] |
| --- | --- |
| 1.37 | 28.63 |
| 2.75 | 19.96 |
| 4.13 | 8.40 |
| 11.78 | 3.56 |
| 12.14 | 2.93 |
| 13.79 | 2.76 |
| 14.54 | 11.08 |
| 14.78 | 8.23 |
| 15.22 | 7.71 |
| 16.23 | 5.60 |
| 16.90 | 8.38 |
| 17.67 | 4.73 |
| 18.38 | 8.22 |
| 18.92 | 100.00 |
| 19.22 | 63.02 |
| 20.37 | 5.98 |
| 21.79 | 2.24 |
| 23.43 | 62.25 |
| 25.12 | 2.46 |
| 26.02 | 2.28 |
| 28.11 | 4.58 |
| 28.39 | 3.40 |
| 29.45 | 3.63 |
| 30.26 | 8.15 |
| 30.85 | 3.48 |
| 32.24 | 5.24 |
| 32.55 | 4.52 |

Figure 3:
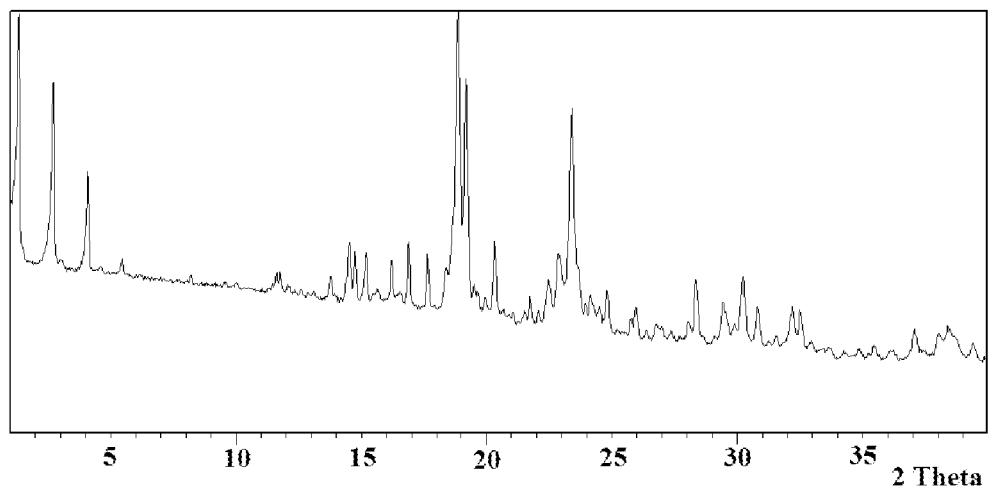
FIG. 3 shows the X-ray powder diffractogram (XRPD) of cocrystal of ubiquinol and 3,5-dihydroxybenzoic acid. The diagram expresses intensity (I; counts) versus angle 2 theta (°).
Figure 4:
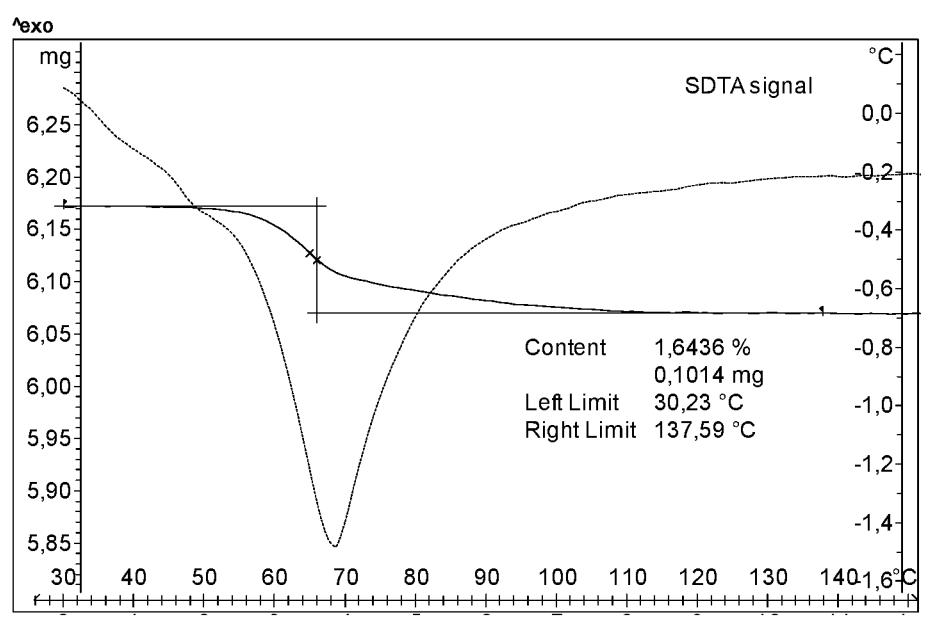
FIG. 4 shows the TGA of cocrystal hydrate of ubiquinol and 3,4-dihydroxybenzoic acid. The thermogram expresses loss weight (% w/w) versus temperature (° C.).

The cocrystal of ubiquinol and 3,5-dihydroxybenzoic acid of the invention may be further characterized by an X-ray diffractogram as in FIG. 3.

In another embodiment, the benzoic acid is 2,5-dihydroxybenzoic acid, and the cocrystal of ubiquinol and 2,5-dihydroxybenzoic acid is characterized by having an X-ray powder diffractogram that comprises characteristic peaks at approximately 1.43, 2.89 and 4.33±0.3 degrees 2 theta (Cu—K$_\alpha$ radiation, $\lambda$=1.5406 Å). In a particular embodiment, the cocrystal of ubiquinol and 2,5-dihydroxybenzoic acid is characterized by having an X-ray powder diffractogram that comprises further characteristic peaks at 14.60, 14.86, 18.82 and 19.05±0.3 degrees 2 theta (Cu—K$_\alpha$ radiation, $\lambda$=1.5406 Å).

More specifically, the cocrystal of ubiquinol and 2,5-dihydroxybenzoic acid of the invention is characterized by exhibiting in the X-ray powder diffractogram a pattern of peaks, expressed in 2 theta units in degrees, 2 (°), which is shown in Table 4.

TABLE 4

List of selected peaks (only peaks with relative intensity greater than or equal to 1% are indicated):

| Pos. [2θ] | Rel. Int. [%] |
|---|---|
| 1.43 | 8.04 |
| 2.89 | 7.89 |
| 4.33 | 5.85 |
| 5.78 | 2.82 |
| 8.20 | 2.52 |
| 9.36 | 2.32 |
| 11.42 | 4.35 |
| 12.80 | 4.24 |
| 13.52 | 4.75 |
| 14.60 | 12 |
| 14.86 | 13.22 |
| 15.26 | 8.73 |
| 17.14 | 5.77 |
| 17.97 | 8.08 |
| 18.82 | 46.01 |
| 19.05 | 100 |
| 20.85 | 4.99 |
| 30.22 | 7.54 |

In another embodiment, the hydrogen bond donor coformer is urea, and the cocrystal of ubiquinol and urea is characterized by having an X-ray powder diffractogram that comprises characteristic peaks at approximately 1.41, 2.89 and 4.36±0.3 degrees 2 theta (Cu—K$_\alpha$ radiation, $\lambda$=1.5406 Å). In a particular embodiment, the cocrystal of ubiquinol and urea is characterized by having an X-ray powder diffractogram that comprises further characteristic peaks at 16.04, 18.97, 20.41 and 23.16±0.3 degrees 2 theta (Cu—K$_\alpha$ radiation, $\lambda$=1.5406 Å).

More specifically, the cocrystal of ubiquinol and urea of the invention is characterized by exhibiting in the X-ray powder diffractogram a pattern of peaks, expressed in 2 theta units in degrees, 2θ (°), which is shown in Table 5.

TABLE 5

List of selected peaks (only peaks with relative intensity greater than or equal to 1% are indicated):

| Pos. [2θ] | Rel. Int. [%] |
|---|---|
| 1.41 | 12.67 |
| 2.89 | 10.8 |
| 4.36 | 4.79 |
| 5.81 | 1.39 |
| 15.44 | 5.33 |
| 16.04 | 6.35 |
| 16.73 | 4.8 |
| 18.97 | 81.93 |
| 20.41 | 7.89 |
| 23.16 | 62.19 |

In another embodiment, the hydrogen bond donor coformer is resorcinol, and the cocrystal of ubiquinol and resorcinol is characterized by having an X-ray powder diffractogram that comprises characteristic peaks at approximately 1.44, 2.91 and 4.38±0.3 degrees 2 theta (Cu—K$_\alpha$ radiation, $\lambda$=1.5406 Å). In an embodiment, the cocrystal of ubiquinol and resorcinol is characterized by having an X-ray powder diffractogram that comprises further characteristic peaks at 18.63, 19.02, 20.15 and 23.00±0.3 degrees 2 theta (Cu—K$_\alpha$ radiation, $\lambda$=1.5406 Å).

More specifically, the cocrystal of ubiquinol and resorcinol of the invention is characterized by exhibiting in the X-ray powder diffractogram a pattern of peaks, expressed in 2 theta units in degrees, 2θ (°), which is shown in Table 6.

TABLE 6

List of selected peaks (only peaks with relative intensity greater than or equal to 1% are indicated):

| Pos. [2θ] | Rel. Int. [%] |
|---|---|
| 1.44 | 18.54 |
| 2.91 | 16.39 |
| 4.38 | 9.88 |
| 5.85 | 4.1 |
| 10.27 | 2.56 |
| 11.57 | 6.66 |
| 12.96 | 2.47 |
| 13.69 | 3.6 |
| 18.63 | 41.54 |
| 19.02 | 100 |
| 20.15 | 14.55 |
| 21.20 | 3.58 |
| 23.00 | 38.93 |

It is also part of the invention the provision of a process for the preparation of the cocrystal of ubiquinol and a hydrogen bond donor coformer, said process comprising the steps of:

a) either preparing a concentrated solution of the hydrogen bond donor coformer in an organic solvent selected from the list consisting of methanol, ethanol, isopropanol, butanol, methyl ethyl ketone, acetone, methyl isobutyl ketone, dimethylformamide, pentane, heptane, cyclohexane, toluene, xylene, ethyl acetate, diethyl ether, tetrahydrofuran, ethylene glycol dimethyl ether, diisopropyl ether, dioxane, dichloromethane, chloroform, acetic acid, benzyl alcohol, formic acid, dimethyl sulfoxide, ethylene glycol, water, aqueous ammonia, diethylamine, and mixtures thereof; and adding ubiquinol until a suspension is observed;

or, alternatively, preparing a concentrated solution of ubiquinol in the organic solvent and adding the hydrogen bond donor coformer until a suspension is observed;

b) stirring the suspension at room temperature until the cocrystal is formed; and c) isolating the cocrystal thus obtained.

In an embodiment, step a) is carried out at room temperature.

In another embodiment, optionally in combination with one or more features of the particular embodiments of the process defined above, the isolation step c) may include removing the organic solvent, for example, by one or more of the following operations: filtration, filtration under vacuum, decantation, and centrifugation, or other suitable techniques as known to a person skilled in the art. Particularly, step c) is carried out by filtration of the solid. In another embodiment, step c) further comprises drying the isolated cocrystal. Particularly, the cocrystal is dried at room temperature, more particularly under vacuum conditions. Generally, the vacuum involves a pressure comprised from 0.5 mbar to 3 mbar.

Particularly, the hydrogen bond donor coformer is selected from the group consisting of an organic carboxylic acid and an organic alcohol. More particularly, the hydrogen bond donor coformer is a benzoic acid such as 3-hydroxybenzoic acid, 3,4-dihydroxybenzoic acid, 3,5-dihydroxybenzoic acid, and 2,5-dihydroxybenzoic acid. Ubiquinol, and the coformers, particularly benzoic acids such as 3-hydroxybenzoic acid, 3,4-dihydroxybenzoic acid, 3,5-dihydroxybenzoic acid, and 2,5-dihydroxybenzoic acid, used as starting materials in the present invention are commercially available.

As an example, the cocrystal of ubiquinol and the benzoic acid may be obtained by:
  a) preparing a concentrated solution of the benzoic acid, such as 3-hydroxybenzoic acid, 3,4-dihydroxybenzoic acid, 3,5-dihydroxybenzoic acid, and 2,5-dihydroxybenzoic acid in the organic solvent as defined above and adding ubiquinol until a suspension is observed;
  b) stirring the suspension at room temperature; and
  c) filtering and drying the solid obtained.

Alternatively, the cocrystal of ubiquinol and the benzoic acid may be obtained by:
  a) preparing a concentrated solution of ubiquinol in the organic solvent and adding a benzoic acid, such as 3-hydroxybenzoic acid, 3,4-dihydroxybenzoic acid, 3,5-dihydroxybenzoic acid, and 2,5-dihydroxybenzoic acid until a suspension is observed;
  b) stirring the suspension at room temperature;
  c) filtering and drying the solid obtained.

As another example, the cocrystal of ubiquinol and urea may be obtained by:
  a) preparing a concentrated solution of ubiquinol in a polar organic solvent, particularly in acetonitrile, and adding urea until a suspension is observed or, alternatively, preparing a concentrated solution of urea in the mentioned polar organic solvent and adding ubiquinol until a suspension is observed;
  b) stirring the suspension at room temperature;
  c) filtering and drying the solid obtained.

As another example, the cocrystal of ubiquinol and resorcinol may be obtained by:
  a) preparing a concentrated solution of ubiquinol in a organic solvent, particularly in dichloromethane, and adding resorcinol until a suspension is observed or, alternatively, preparing a concentrated solution of resorcinol in the mentioned organic solvent and adding ubiquinol until a suspension is observed;
  b) stirring the suspension at room temperature;
  c) filtering and drying the solid obtained.

In an embodiment, the organic solvent is a polar organic solvent.

In another particular embodiment, the benzoic acid is 3-hydroxybenzoic acid and the organic solvent is selected from the group consisting of acetonitrile, xylene, ethyl acetate and butanol. Particularly, the solvent is acetonitrile.

In a particular embodiment, the benzoic acid is 3,4-dihydroxybenzoic acid and the organic solvent is selected from the group consisting of butanol, ethyl acetate, diethyl ether and acetone. Particularly, the solvent is butanol.

In another particular embodiment, the benzoic acid is 3,5-dihydroxybenzoic acid and the organic solvent is selected from the group consisting of acetonitrile, methyl ethyl ketone, diethyl ether, butanol, methyl isobutyl ketone, benzyl alcohol, and formic acid. Particularly, the solvent is acetonitrile.

In another particular embodiment, the benzoic acid is 2,5-dihydroxybenzoic acid and the organic solvent is ethyl acetate.

In a particular embodiment, the molar ratio between 3-hydroxybenzoic acid and ubiquinol is 1:1.

In another particular embodiment, the molar ratio between 3,5-dihydroxybenzoic and ubiquinol is 1:1.

In still another particular embodiment, the cocrystal of ubiquinol and 3,4-dihydroxybenzoic acid is a hydrate with a 1.6%±0.1% water content according to TGA analysis. Water forming part of the mentioned cocrystal is taken either from the water contained in the solvent or from atmospheric humidity.

Particularly, in any one of the processes above the stirring is carried out for 10 to 20 hours.

The cocrystals of ubiquinol and a hydrogen bond donor coformer as defined above the invention may also be defined by its preparation process. Accordingly, this aspect of the invention can be formulated as the cocrystals of ubiquinol and a hydrogen bond donor coformer as defined above obtainable by the previous process, optionally including any preferred or particular embodiment of the processes and possible combinations of some of the process features disclosed above.

The second aspect of the invention relates to a composition comprising an effective amount of a cocrystal of ubiquinol and a hydrogen bond donor coformer as defined above together with one or more appropriate acceptable excipients or carriers.

The term "effective amount" refers to the amount of the cocrystal that provides a therapeutic effect after its application.

In an embodiment, the composition of the second aspect of the invention is a pharmaceutical composition comprising a pharmaceutically effective amount of a cocrystal of ubiquinol and a hydrogen bond donor coformer as defined above together with one or more appropriate pharmaceutically acceptable excipients or carriers. The term "pharmaceutical composition" refers to a mixture of a cocrystal disclosed herein with other chemical components, such as diluents or carriers. The pharmaceutical composition facilitates administration of the cocrystal to an organism. Particularly, the pharmaceutical composition can be formulated for inhaled, intramuscular, subcutaneous, oral, or topical, administration.

In an embodiment, the composition of the second aspect of the invention is a dietary supplement comprising an effective amount of a cocrystal of ubiquinol and a hydrogen bond donor coformer as defined above together with one or more appropriate orally acceptable excipients or carriers. The term "dietary supplement" refers to a product taken orally that contains an ingredient intended to supplement the diet. Dietary supplements can be in form of tablets, capsules, softgels, gelcaps, liquids, powders, bars, drinks, shakes and other food products. As an example, the dietary supplement may be to enhance athletic performance.

The terms "acceptable excipients or carriers" refers to acceptable material, composition or vehicle, such as liquid or solid filler, diluent, excipient, solvent, or encapsulating material. Each component must be acceptable in the sense of being compatible with the other ingredients of the composition. It must also be suitable for use in contact with the tissue or organ of humans and animals without excessive toxicity, irritation, allergic response, immunogenicity or other problems or complications commensurate with a reasonable benefit/risk ratio. In pharmaceutical compositions the acceptable excipient or carrier is a pharmaceutically acceptable excipient or carrier.

In a particular embodiment, the pharmaceutical composition as defined above further comprises one or more active ingredients selected from the group consisting of cardiovascular agents, antilipemic agents, antidiabetic agents, and antiplatelet agents. In a particular embodiment, the dietary supplement as defined above further comprises one or more active ingredients selected from the group consisting of L-carnitine, xylitol, vitamins, carotenoids, flavonoids, copper, zinc, and manganese.

Examples of cardiovascular agents include, but would not be limited to, alpha andrenergic agonists such as adrafinil, adrenalone, amidephrine, apraclonidine, budralazine, clonidine, cyclopentamine, dexmedetomidine, dimetofrine, dipivefrin, ecabapide, ephedrine, epinephrine, fenoxazoline, guanabenz, guanfacine, hydroxyamphetamine, ibopamine, indanazoline, isometheptene, mephentermine, metaraminol, methoxamine, methylhexaneamine, midodrine, mivazerol, modafinil, moxonidine, naphazoline, norepinephrine, norfenefrine, octodrine, octopamine, oxymetazoline, phenylephrine, hydrochloride, phenylpropanolamine, phenylpropyl methylamine, pholedrine, propylhexedrine, pseudoephedrine, rilmenidine, synephrine, talipexole, tetrahydrozoline, tiamenidine, tramazoline, tuaminoheptane, tymazoline, tyramine, and xylometazoline; beta andrenergic agonists such as albuterol, bambuterol, bitolterol, carbuterol, clenbuterol, clorprenaline, denopamine, dixoethedrine, dopexamine, ephedrine, epinephrine, etafedrine, ethylnorepinephrine, fenoterol, formoterol, hexoprenaline, Ibopamine, isoetharine, isoproterenol, methoxyphenamine, mabuterol, metaproterenol, oxyfedrine, pirbuterol, prenalterol, procaterol, protokylol, reproterol, rimiterol, ritodrine, salmeterol, soterenol, terbutaline, tretoquinol, tulobuterol, and xamoterol; alpha andrenergic blockers such as amosulalol, arotinolol, dapiprazole, doxazosin, ergoloid mesylates, fenspiride, Idazoxan, Indoramin, labetalol, monatepil, naftopidil, nicergoline, prazosin, tamsulosin, terazosin, tolazoline, trimazosin and yohimbine; beta andrenergic blockers such as acebutolol, alprenolol, amosulalol, arotinolol, atenolol, befunolol, betaxolol, bevantolol, bisoprolol, bopindolol, bucindolol, bucumolol, bufetolol, bufuralol, bunitrolol, bupranolol, butidrine hydrochloride, butofilol, carazolol, carteolol, carvedilol, celiprolol, cetamolol, cloranolol, dilevalol, esmolol, Indenolol, labetalol, landiolol, levobunolol, mepindolol, metipranolol, metoprolol, moprolol, nadolol, nadoxolol, nebivolol, nifenalol, nipradilol, oxprenolol, penbutolol, pindolol, practolol, pronethalol, propanolol, sotalol, sulfinalol, talinolol, tertatolol, tilisolol, timolol, toliprolol and xibenolol; antiarrhythmics such as acebutolol, acecainide, adenosine, ajmaline, alprenolol, amiodarone, aprindine, arotinolol, atenolol, azimilide, bevantolol, bidisomide, bretylium tosylate, bucumolol, bufetolol, bunaftine, bunitrolol, bupranolol, butidrine hydrochloride, butobendine, capobenic acid, carazolol, carteolol, cifenline, cloranolol, disopyramide, dofetilide, encainide, esmolol, flecainide, hydroquinidine, Ibutilide, Indecainide, Indenolol, ipratropium bromide, landiolol, lidocaine, lorajmine, lorcainide, meobentine, mexiletine, moricizine, nadoxolol, nifenalol, oxprenolol, penbutolol, pentisomide, pilsicainide, pindolol, pirmenol, practolol, prajmaline, procainamide hydrochloride, pronethalol, propafenone, propranolol, pyrinoline, quinidine, sematilide, sotalol, talinolol, tedisamil, tilisolol, timolol, tocainide, verapamil and xibenolol; calcium channel blockers such as arylalkylamines: bepridil, clentiazem, diltiazem, fendiline, gallopamil, mibefradil, prenylamine, semotiadil, terodiline, verapamil; dihydropyridine derivatives such as amlodipine, aranidipine, bamidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, piperazine derivatives such as cinnarizine, dotarizine, flunarizine, lidoflazine, lomerizine; and others such as bencyclane, etafenone, fantofarone, monatepil, and perhexiline; vasodilators such as amotriphene, benfurodil hemisuccinate, benziodarone, chloracizine, chromonar, clobenfurol, clonitrate, cloricromen, dilazep, droprenilamine, efloxate, erythrityl tetranitrate, etafenone, fendiline, hexestrol bis ([β-diethylaminoethyl) ether, hexobendine, Itramin tosylate, khellin, lidoflazine, mannitol hexanitrate, nitroglycerin, pentaerythritol tetranitrate, pentrinitrol, perhexiline, pimefylline, prenylamine, propatyl nitrate, trapidil, tricromyl, trimetazidine, trolnitrate phosphate and visnadine; vasopressors such as antihypotensive: amezinium methyl sulfate, angiotensin amide, dopamine, dimetofrine, etifelmin, etilefrin, gepefrine, metaraminol, methoxamine, midodrine, norepinephrine, pholedrine and synephrine; and inotropic agents such as digoxin, milrinone, dobutamine, and dopamine.

Examples of antilipemic agents include, but would not be limited to, bile acid sequesterants such as cholestyramine resin, cholesevelam hydrochloride, colestipol, and polidexide; fibric acid derivatives such as bezafibrate, binifibrate, ciprofibrate, clinofibrate, clofibrate, clofibric acid, etofibrate, fenofibrate, gemfibrozil, pirifibrate, ronifibrate, simfibrate and theofibrate; hmg coa reductase inhibitors such as atorvastatin, cerivastatin, fluvastatin, lovastatin, pravastatin sodium, pitavastatin, rosuvastatin and simvastatin; omega-3-fatty acids such as eicosapentaenoic acid, docosahexaenoic acid, and docosapentaenoic acid; and nicotidine acid derivatives such as acipimox, aluminum nicotinate, niceritrol, nicoclonate, nicomol, and oxiniacic acid; and other antilipemic agents such as acifran, benfluorex, β-benzalbutyramide, carnitine, chonodroitin sulfate, clomestrone, detaxtran, dextran sulfate sodium, eicosapentaenoic acid, eritadenine, ezetimibe, furazabol, meglutol, melinamide, u-oryzanol, pantethine, pentaerythritol tetraacetate, α-phenylbutyramide, pirozadil, probucol, resveratrol, β-sitosterol, sultosilic acid, tiadenol, triparanol, and xenbucin.

Examples of antidiabetic agents include, but would not belimited to, biguanides (i.e., metformin, buformin, phenformin), sulfonylureas (i.e., acetohexamide, carbutamide, chlorpropamide, glibomuride, gliclazide, glimepiride, glipizide, gliquidone, glisoxepid, glyburide, glybuthiazole, glybuzole, glyhexamide, glymidine, glypinamide, phenbutamide, tolazamide, tolbutamide, tolcyclomide), thiazolidinediones (i.e., pioglitazone, rosiglitazone, troglitazone), beta andrenergic blockers, and other antidiabetics such as acarbose, calcium mesoxalate, miglitol, nateglinide, repaglinide, voglibose.

Examples of antiplatelet agents include, but would not be limited to, tirofiban, dipyridamole, anagrelide, epoprostanol, eptifibatide, clopidrogel, cilostazole and triclopidine.

Examples of vitamins include but are not limited to Vitamin A (acetate or palmitate, betacarotene), vitamin B1 (thiamine (aneurine)) (hydrochloride or mononitrate), B2 (riboflavin), vitamin B6 (pyridoxine hydrochloride), vitamin B12 (cobalamin), vitamin B12 (cyanocobalamin), vitamin B12 (mecobalamin), vitamin C (ascorbic acid), nicotinic acid, vitamin D2 (ergo-calciferol), vitamin D3 (cholecalciferol), vitamin E (alpha tocopheryl acetate, alpha tocopheryl succinate, alpha tocopherol, γ-tocopherol), vitamin K (phylloquinone, menadione etc), and nicotinamide riboside.

Examples of carotenoids include, but are not limited to, lutein, lycopene, α-carotene, β-carotene, γ-carotene, β-cryptoxanthin, Capsanthin, Zeaxanthin, Astaxanthin.

Examples of flavonoids include, but are not limited to, kaempferol, myricetin, quercetin, rutin, catechin, epicatechin, ECG, gallocatechin, EGC, EGCG, cyanidin, caffeic acid, theaflavin, theaflavin gallate, luteolin, daidzein, genestein, and glycitein.

The compositions of the present invention can be prepared according to methods well known in the state of the art. The appropriate excipients and/or carriers, and their amounts, can readily be determined by those skilled in the art according to the type of formulation being prepared.

All the embodiments disclosed above for the cocrystals of ubiquinol as defined above also applies to the compositions of the invention.

The third aspect of the invention relates to a cocrystal of ubiquinol and a hydrogen bond donor coformer as defined above for use as a medicament.

Particularly, the cocrystal of ubiquinol and a hydrogen bond donor coformer as defined above is for use in the prophylaxis and/or treatment of CoQ10 deficiencies, gingivitis, heart failure, angina, mitochondrial disorders, fibromyalgia, cardiovascular disease, atherosclerosis, dyslipidemia, hypertension, diabetes, cancer, and neurological conditions such as Parkinson's disease, Huntington's disease, Alzheimer's disease, infertility, and Friedreich's ataxia. This aspect could be also formulated as the use of the a cocrystals of ubiquinol and a hydrogen bond donor coformer, such as a benzoic acid as defined above, for the preparation of a medicament for the prophylaxis and/or treatment of CoQ10 deficiencies, gingivitis, heart failure, angina, mitochondrial disorders, fibromyalgia, cardiovascular disease, atherosclerosis, dyslipidemia, hypertension, diabetes, cancer, and neurological conditions such as Parkinson's disease, Huntington's disease, Alzheimer's disease, infertility, and Friedreich's ataxia. It also relates to a method for the prophylaxis and/or treatment of a mammal suffering, or susceptible to suffer, from CoQ10 deficiencies, gingivitis, heart failure, angina, mitochondrial disorders, fibromyalgia, cardiovascular disease, atherosclerosis, dyslipidemia, hypertension, diabetes, cancer, and neurological conditions such as Parkinson's disease, Huntington's disease, Alzheimer's disease, infertility, and Friedreich's ataxia, wherein the method comprises administering to said mammal an effective amount of the cocrystal of ubiquinol and a hydrogen bond donor coformer as defined above, together with one or more acceptable excipients or carriers.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Reference signs related to drawings and placed in parentheses in a claim, are solely for attempting to increase the intelligibility of the claim, and shall not be construed as limiting the scope of the claim. Furthermore, the present invention covers all possible combinations of particular and preferred embodiments described herein.

EXAMPLES

General Considerations

Ubiquinol is commercially available by BOC Sciences, 3-Hydroxybenzoic acid, 3,4-dihydroxybenzoic acid, 3,5-dihydroxybenzoic acid, and 2,5-dihydroxybenzoic acid are commercially available by Sigma-Aldrich.

Powder X-Ray diffraction (PXRD) analyses were performed by sandwiching the powder samples between polyester films of 10 micrometres of thickness or polyamide (kapton) films of 15 micrometres of thickness and analysed in a PANalytical X'Pert PRO MPD q/q powder diffractometer of 240 millimetres of radius, in a configuration of convergent beam with a focalizing mirror and a flat sample transmission geometry, in the following experimental conditions: Cu Kα radiation ($\lambda$=1.5406 Å); Work power: 45 kV and 40 mA; Incident beam slits defining a beam height of 0.4 millimetres; Incident and diffracted beam 0.02 radians Soller slits; PIXcel detector: Active length=3.347°; 2θ/θ scans from 2 to 40° 2θ with a step size of 0.026° 2θ and a measuring time of 76 seconds per step.

Thermogravimetric analysis (TGA) was performed on a Mettler-Toledo TGA-851e thermobalance. Experimental conditions: alumina crucibles of 70 μL volume, atmosphere of dry nitrogen with 50 mL/min flow rate, heating rate of 10° C./min.

Example 1.—Preparation of a Cocrystal of Ubiquinol and 3-Hydroxybenzoic Acid (P58-VI)

A concentrated solution of 3-hydroxybenzoic acid (of 100 mg) in acetonitrile (1.25 mL) was prepared. Ubiquinol was added until suspension was observed. The suspension was stirred overnight at room temperature. The solid was filtered and dried under vacuum. (m.p.: 58.8° C.). The same cocrystal was also obtained by reaction crystallization in butanol instead that acetonitrile.

According to its $^1$H-NMR, it could be attributed to a new form containing 1 molecule of 3-hydroxybenzoic acid per molecule of P58.

Example 2.—Preparation of a Cocrystal Hydrate of Ubiquinol and 3,4-dihydroxybenzoic Acid (P58-III)

A concentrated solution of ubiquinol (50 mg) in butanol (0.8 mL) was prepared. 3,4-dihydroxybenzoic acid was added to the solution until suspension was observed. The suspension was stirred overnight at room temperature. The solid was filtered and dried under vacuum. The same cocrystal was also obtained by reaction crystallization in AcOEt instead of butanol.

DSC shows two consecutive endothermic processes corresponding to loss of water together with melting (onset: 45.4° C.). Water stoichiometry has been deduced from TGA analysis (1.64%, onset: 30.2° C.). Water forming part of the cocrystal of the title is taken either from the water contained in the solvent or from atmospheric humidity.

As shown in Table 7 below, molar ratio [1:1:1] of ubiquinol 3,4-dihydroxybenzoic acid monohydrate cocrystal was confirmed by elemental analysis.

TABLE 7

| Element | Theoretical elemental analysis (%) Molar ratio | | Experimental elemental analysis (%) |
|---|---|---|---|
| | [2:1:1] | [1:1:1] | |
| C | 78.90 | 76.41 | 76.07 |
| H | 10.17 | 9.72 | 10.53 |
| O | 10.93 | 13.88 | 13.40 |

Example 3.—Preparation of a Cocrystal of Ubiquinol and 3,5-dihydroxybenzoic Acid (P58-V)

A concentrated solution of 3,5-dihydroxybenzoic acid (100 mg) in acetonitrile (in 0.8 mL) was prepared. Ubiquinol was added until suspension was observed. The suspension was stirred overnight at room temperature. The solid was filtered and dried under vacuum. (m.p.: 66.0° C.). The same cocrystal was also obtained by reaction crystallization in methyl ethyl ketone or in $Et_2O$ instead of acetonitrile.

As shown in Table 8 below, molar ratio [1:1] has been confirmed by elemental analysis in ubiquinol 3-hydroxybenzoic acid cocrystal.

TABLE 8

| Element | Theoretical elemental analysis (%) Molar ratio | | Experimental elemental analysis (%) |
|---|---|---|---|
| | [2:1] | [1:1] | |
| C | 80.34 | 79.00 | 78.84 |
| H | 10.25 | 9.84 | 10.51 |
| O | 9.42 | 11.16 | 10.65 |

Example 4.—Preparation of a Cocrystal of Ubiquinol and 2,5-dihydroxybenzoic Acid A concentrated solution of ubiquinol (100 mg) in ethyl acetate (in 0.2 mL) was prepared. 2,5-dihydroxybenzoic acid was added until suspension was observed. The suspension was stirred overnight at room temperature. The solid was filtered and dried under vacuum.

Example 5.—Preparation of a Cocrystal of Ubiquinol and Urea

A concentrated solution of urea (20 mg) in isopropanol (in 0.6 mL) was prepared. Ubiquinol was added until suspension was observed. The suspension was stirred overnight at room temperature. The solid was filtered and dried under vacuum.

Example 6.—Preparation of a Cocrystal of Ubiquinol and Resorcinol

A concentrated solution of resorcinol (500 mg) in dichloromethane (in 0.5 mL) was prepared. Ubiquinol was added until suspension was observed. The suspension was stirred overnight at room temperature. The solid was filtered and dried under vacuum.

Example 7.—Preparation of Ubiquinol:Benzyl Alcohol (P58-G)

The compound ubiquinol:benzyl alcohol was obtained by reaction crystallization in benzyl alcohol or ethanol and in drop grinding of ubiquinol with benzyl alcohol. According to its $^1$H-NMR and TGA, it could be attributed to a new form containing 1 molecule of benzyl alcohol per molecule of ubiquinol.

Example 8.—Stability Study—Comparative Ubiquinol Vs Cocrystals in Different Conditions The stability of the different forms has been studied under two experimental conditions. The samples were stored under both conditions inside a Series FD Binder chamber and they were analyzed periodically:

condition A: 25° C. and 57% of relative humidity;

condition B: 40° C. and 75% of relative humidity.

A saturated solution of sodium bromide salt (57% RH) and a saturated solution of sodium chloride (75% RH) were used to control relative humidity. Table 9 shows the stability at 25° C. measured by controlling the moment when ubiquinone was detected.

TABLE 9

| Sample | 25° C.* | 25° C.-57% HR |
|---|---|---|
| Ubiquinol | <50 days | <26 days |
| P58-III | >133 days | >551 days |
| P58-VI | >64 days | >434 days |

*Relative humidity was not controlled;
"<" indicates that ubiquinone was detected at least after the indicated number of days;
">" indicates that ubiquinone has not been detected yet.

Tables 10 and 11 shows the stability at 25° C., 57% HR and at 40° C. 75% HR by indicating the form detected after the mentioned days. No ubiquinone was detected at least after 14 days.

TABLE 10

| | 25° C.-57% HR | | 40° C.-75% HR | |
|---|---|---|---|---|
| Time | P58-III-B | P58-VI | P58-III-B | P58-VI |
| 0 | P58-III | P58-VI | P58-III | P58-VI |
| 7 days | P58-III | P58-VI | P58-III | P58-VI |
| 14 days | P58-III | P58-VI | P58-III | P58-VI |
| 51 days | P58-III | P58-VI | P58-III | Ubiquinone[1] |
| 84 days | P58-III | — | P58-III and Ubiquinone↓ | — |
| 119 days | P58-III | P58-VI | Ubiquinone and P58-III↓↓↓ | —[2] |
| 235 days | P58-III | — | Ubiquinone | — |
| 288 days | — | P58-VI | —[2] | — |
| 405 days | P58-III | — | — | — |
| 435 days | P58-III | P58-VI[1] | — | — |
| 551 days | P58-III[1] | — | — | — |

[1]low crystallinity.
[2]The sample absorbed moisture showing liquid texture.

TABLE 11

| Time (days) | 25° C.-57% HR | 40° C.-75% HR |
|---|---|---|
| 0 | Form A | Form A |
| 7 | Form A | Form B |
| 14 | mixture Form A and Form B | —[1] |
| 26 | mixture Form B and Ubiquinone | — |
| 37 | mixture Form B and Ubiquinone | — |
| 62 | mixture Form B and Ubiquinone[2] | — |
| 130 | mixture Form B and Ubiquinone | — |
| 300 | mixture Form B and Ubiquinone | — |
| 446 | Ubiquinone (low crystallinity) | — |

*The sample absorbed moisture showing a liquid texture. It was placed at room conditions (23° C.-30% HR) and the sample was dehydrated and a solid crystallized after 2 hours. Its XPRD shows the Form B with low crystallinity.
[2]The sample was analyzed by $^1$H-NMR and confirms the presence of Ubiquinone in a 2:3 molar ratio (Ubiquinol:Ubiquinone).

The stability of cocrystal P58-V is expected to be similar to cocrystal P58-III.

Example 9.—Preparation of Amorphous Form of Ubiquinol

The amorphous ubiquinol has been detected through a quenching from the melt experiment in a DSC equipment (Mettler Toledo 822 with Aluminum crucibles). The glass transition midpoint has been determined between −68° C. and −60° C. for several heating rates between 2 and 20° C./min.

CITATION LIST

1. US2015284311A1

The invention claimed is:

1. A cocrystal of ubiquinol and a hydrogen bond donor coformer,
   wherein the hydrogen bond donor coformer is selected from the group consisting of 3-hydroxybenzoic acid and 3,4-dihydroxybenzoic acid,
   wherein in the cocrystal of ubiquinol and 3-hydroxybenzoic acid, the molar ratio of ubiquinol and 3-hydroxybenzoic acid is 1:1;
   wherein the cocrystal of ubiquinol and 3,4-dihydroxybenzoic acid is a hydrate; and
   wherein in the cocrystal of ubiquinol and 3,4-dihydroxybenzoic acid, the molar ratio of ubiquinol, 3,4-dihydroxybenzoic acid, and water is 1:1:1.

2. The cocrystal according to claim 1, wherein the hydrogen bond donor coformer is 3-hydroxybenzoic acid, and which is characterized by having an X-ray powder diffractogram that comprises characteristic peaks at 1,36, 2.74, 4.12, 17.04, 17.81, 19.30 and 23.28±0.3 degrees 2 theta with Cu-K$_\alpha$ radiation, λ=1.5406 Å.

3. The cocrystal according to claim 1, wherein the hydrogen bond donor coformer is 3,4-dihydroxybenzoic acid, and which is characterized by having an X-ray powder diffractogram that comprises characteristic peaks at 1.34, 2.69, 4.04, 14.60, 17.29, and 18.06±0.3 degrees 2 theta with Cu-K$_\alpha$ radiation, λ=1.5406 Å.

4. The cocrystal according to claim 3, which is a hydrate with a 1.6%±0.1% water content according to TGA analysis.

5. A composition comprising an effective amount of the cocrystal of ubiquinol and a hydrogen bond donor coformer as defined in claim 1 together with one or more appropriate acceptable excipients or carriers.

6. The composition according to claim 5, which is a pharmaceutical composition or a dietary supplement.

7. The composition according to claim 6, which is a pharmaceutical composition further comprising one or more active ingredients selected from the group consisting of cardiovascular agents, antilipemic agents, antidiabetic agents, and antiplatelet agents.

8. The composition according to claim 6, which is a dietary supplement further comprising one or more active ingredients selected from the group consisting of L-carnitine, xylitol, vitamins, carotenoids, flavonoids, copper, zinc, and manganese.

9. A composition comprising an effective amount of the cocrystal of ubiquinol and a hydrogen bond donor coformer as defined in claim 3 together with one or more appropriate acceptable excipients or carriers.

10. A composition comprising an effective amount of the cocrystal of ubiquinol and a hydrogen bond donor coformer as defined in claim 4 together with one or more appropriate acceptable excipients or carriers.

11. The composition according to claim 9, which is a pharmaceutical composition or a dietary supplement.

12. The composition according to claim 10, which is a pharmaceutical composition or a dietary supplement.

13. The composition according to claim 9, which is a pharmaceutical composition further comprising one or more active ingredients selected from the group consisting of cardiovascular agents, antilipemic agents, antidiabetic agents, and antiplatelet agents.

14. The composition according to claim 10, which is a pharmaceutical composition further comprising one or more active ingredients selected from the group consisting of cardiovascular agents, antilipemic agents, antidiabetic agents, and antiplatelet agents.

15. The composition according to claim 9, which is a dietary supplement further comprising one or more active ingredients selected from the group consisting of L-carnitine, xylitol, vitamins, carotenoids, flavonoids, copper, zinc, and manganese.

16. The composition according to claim 10, which is a dietary supplement further comprising one or more active ingredients selected from the group consisting of L-carnitine, xylitol, vitamins, carotenoids, flavonoids, copper, zinc, and manganese.

* * * * *